US009050455B2

(12) United States Patent
Olsen et al.

(10) Patent No.: US 9,050,455 B2
(45) Date of Patent: Jun. 9, 2015

(54) TRANSVERSE TRIPOLE NEUROSTIMULATION METHODS, KITS AND SYSTEMS

(75) Inventors: James M. Olsen, Fridley, MN (US); Gary W. King, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 3028 days.

(21) Appl. No.: 11/256,220

(22) Filed: Oct. 21, 2005

(65) Prior Publication Data

US 2006/0122678 A1  Jun. 8, 2006

Related U.S. Application Data

(60) Provisional application No. 60/621,007, filed on Oct. 21, 2004.

(51) Int. Cl.
*A61N 1/00* (2006.01)
*A61N 1/05* (2006.01)
*A61N 1/36* (2006.01)

(52) U.S. Cl.
CPC ........... *A61N 1/0551* (2013.01); *A61N 1/36017* (2013.01); *A61N 1/36021* (2013.01); *A61N 1/3605* (2013.01)

(58) Field of Classification Search
CPC ............ A61N 1/0551; A61N 1/36017; A61N 1/36021; A61N 1/3605; A61N 1/0553; A61N 1/0558
USPC .................................................. 607/117, 46
See application file for complete search history.

(56) References Cited

U.S. PATENT DOCUMENTS

| | | | |
|---|---|---|---|
| 3,822,708 A | | 7/1974 | Zilber |
| 5,417,719 A | * | 5/1995 | Hull et al. ........................ 607/46 |
| 5,501,703 A | | 3/1996 | Holsheimer et al. |
| 5,643,330 A | | 7/1997 | Holsheimer et al. |
| 5,713,922 A | | 2/1998 | King |
| 5,849,033 A | | 12/1998 | Mehmanesh et al. |
| 5,895,416 A | * | 4/1999 | Barreras et al. ................. 607/62 |
| 5,925,070 A | | 7/1999 | King et al. |
| 6,002,964 A | | 12/1999 | Feler et al. |
| 6,052,624 A | | 4/2000 | Mann |
| 6,083,252 A | | 7/2000 | King et al. |
| 6,104,957 A | | 8/2000 | Alo et al. |

(Continued)

FOREIGN PATENT DOCUMENTS

| EP | 1514576 | 3/2005 |
|---|---|---|
| EP | 1257320 | 6/2005 |

(Continued)

OTHER PUBLICATIONS

Wilbert A. Wesselink, PhD. Jan Holsheimer, PhD et al. Quantitative Aspects of the Clinical Performance of Transverse Tripolar Spinal Cord Stimulation, Neuromodulation, vol. 2, No. 1, 1999, pp. 5-14.

*Primary Examiner* — Christopher D Koharski
*Assistant Examiner* — Roland Dinga

(57) ABSTRACT

An implantable neurostimulation lead kit adapted for tripolar electric simulation and/or field steering using percutaneously implantable electric stimulation leads. The kit includes three electric stimulation leads that are adapted to provide an electrode array defining, for example, a plurality of electrode sets that may be used to provide tripolar stimulation and/or electric field steering. A method of electrically stimulating the spinal cord is also described.

15 Claims, 12 Drawing Sheets

(56) References Cited

U.S. PATENT DOCUMENTS

| | | | |
|---|---|---|---|
| 6,161,047 A | 12/2000 | King et al. |
| 6,236,892 B1 | 5/2001 | Feler |
| 6,292,702 B1 | 9/2001 | King et al. |
| 6,319,241 B1 | 11/2001 | King et al. |
| 6,393,325 B1 | 5/2002 | Mann et al. |
| 6,442,435 B2 | 8/2002 | King et al. |
| 6,505,078 B1 | 1/2003 | King et al. |
| 6,587,724 B2 | 7/2003 | Mann |
| 6,587,733 B1 | 7/2003 | Cross, Jr. et al. |
| 6,609,031 B1 | 8/2003 | Law et al. |
| 6,609,032 B1 | 8/2003 | Woods et al. |
| 6,714,822 B2 | 3/2004 | King et al. |
| 6,745,079 B2 | 6/2004 | King |
| 6,795,737 B2 | 9/2004 | Gielen et al. |
| 6,895,283 B2 | 5/2005 | Erickson et al. |
| 6,909,917 B2 | 6/2005 | Woods et al. |
| 6,909,918 B2 | 6/2005 | Stypulkowski |
| 6,993,384 B2 | 1/2006 | Bradley et al. |
| 2001/0023367 A1 | 9/2001 | King et al. |
| 2001/0053885 A1 | 12/2001 | Gielen et al. |
| 2002/0055762 A1 | 5/2002 | Gliner |
| 2002/0151948 A1 | 10/2002 | King et al. |
| 2003/0018370 A1 | 1/2003 | King et al. |
| 2003/0055476 A1 | 3/2003 | Vinup et al. |
| 2003/0088301 A1 | 5/2003 | King |
| 2004/0034394 A1 | 2/2004 | Woods et al. |
| 2004/0186543 A1 | 9/2004 | King et al. |
| 2004/0186544 A1 | 9/2004 | King |
| 2005/0096718 A1 * | 5/2005 | Gerber et al. ............... 607/117 |
| 2005/0203599 A1 | 9/2005 | Garabedian et al. |
| 2005/0209667 A1 | 9/2005 | Erickson et al. |
| 2005/0222626 A1 | 10/2005 | DiLorenzo |
| 2005/0240241 A1 | 10/2005 | Yun et al. |
| 2005/0240242 A1 | 10/2005 | DiLorenzo |
| 2005/0283201 A1 | 12/2005 | Machado et al. |
| 2006/0004422 A1 | 1/2006 | DeRidder |
| 2006/0009815 A1 | 1/2006 | Boveja et al. |
| 2006/0009820 A1 | 1/2006 | Royle |
| 2006/0017575 A1 | 1/2006 | McAdams |

FOREIGN PATENT DOCUMENTS

| | | |
|---|---|---|
| WO | WO 95/19603 | 7/1995 |
| WO | WO 99/55411 | 11/1999 |
| WO | WO 01/24872 | 4/2001 |
| WO | WO 02/30509 | 4/2002 |
| WO | WO2005/089961 | 9/2005 |
| WO | WO 2006/010025 | 1/2006 |
| WO | WO2006/017277 | 2/2006 |

* cited by examiner

Table A - Voltage Controlled Stimulation

| | L0 | L1 | L2 | L3 | C0 | C1 | C2 | C3 | C4 | C5 | C6 | C7 | R0 | R1 | R2 | R3 |
|---|---|---|---|---|---|---|---|---|---|---|---|---|---|---|---|---|
| Electrode configuration of figure 6 | 4V | | | | 0V | | | | | | | | 4V | | | |
| Electrode configuration of figure 9 | 4V | | | | | 0V | | | | | | | 4V | | | |
| Electrode configuration of figure 13 | 2V | | | | 0V | | | | | | | | 5V | | | |
| Electrode configuration of figure 11 | 4V | | | | | 0V | 0V | | | | | | | 4V | | |
| Electrode configuration of figure 15 | 2V | 2V | | | | 0V | 0V | | | | | | 5V | 5V | | |

FIG. 17

Table B - Voltage Controlled Stimulation (with cathodal voltage less than IPG shield voltage)

| | L0 | L1 | L2 | L3 | C0 | C1 | C2 | C3 | C4 | C5 | C6 | C7 | R0 | R1 | R2 | R3 |
|---|---|---|---|---|---|---|---|---|---|---|---|---|---|---|---|---|
| Electrode configuration of figure 6 | 2V | | | | -2V | | | | | | | | 2V | | | |
| Electrode configuration of figure 9 | 2V | | | | -2V | -2V | | | | | | | 2V | | | |
| Electrode configuration of figure 13 | 1V | | | | -1V | | | | | | | | 2.5V | | | |
| Electrode configuration of figure 11 | 2V | | | | | -2V | -2V | | | | | | | 2V | | |
| Electrode configuration of figure 15 | 1V | 1V | | | | -1V | -1V | | | | | | 2.5V | 2.5V | | |

FIG. 18

Table C - Current Controlled Stimulation

| | L0 | L1 | L2 | L3 | C0 | C1 | C2 | C3 | C4 | C5 | C6 | C7 | R0 | R1 | R2 | R3 |
|---|---|---|---|---|---|---|---|---|---|---|---|---|---|---|---|---|
| Electrode configuration of figure 7 | +5ma | | | | -10ma | | | | | | | | +5ma | | | |
| Electrode configuration of figure 10 | +5ma | | | | -5ma | -5ma | | | | | | | +5ma | | | |
| Electrode configuration of figure 14 | +3ma | | | | -10ma | | | | | | | | +7ma | | | |
| Electrode configuration of figure 12 | +5ma | | | | | -5ma | -5ma | | | | | | | +5ma | | |
| Electrode configuration of figure 16 | +3ma | +3ma | | | | -5ma | -5ma | | | | | | +7ma | +7ma | | |

FIG. 19

TRANSVERSE TRIPOLE NEUROSTIMULATION METHODS, KITS AND SYSTEMS

RELATED APPLICATION

This application claims priority to provisional U.S. Application Ser. No. 60/621,007, filed Oct. 21, 2004, the entire contents of which are incorporated herein by reference.

FIELD

This application relates to electrical stimulation of biological tissue, and more particularly to methods and systems for neurostimulation, for example, of the spinal cord with a tripole orientated generally transverse to the axis of the spinal cord.

BACKGROUND

Transverse tripole stimulation ("TTS") may involve, for example, at least three electrodes arranged substantially along a line approximately perpendicular or otherwise transverse to the axis of the spinal cord. The electrical field can be steered from side to side by varying the current or voltage between the center electrode and the outer electrodes. Voltages or currents can be in phase (overlapping in time) or out of phase between the right and left side. Using the outer electrodes as anodes may prevent nerve root stimulation.

See, e.g., U.S. Pat. Nos. 5,501,703; 5,643,330 and 5,895,416.

BRIEF SUMMARY

As used herein, the term, "exemplary" is used in the sense of "for example" or "for purposes of illustration," and not in a limiting sense.

A first exemplary embodiment is a neurostimulation lead kit that generally comprises first, second and third electric stimulation leads. Each lead has a distal end portion and a plurality of stimulation electrodes spaced apart along the distal end portion thereof. The stimulation electrodes of the first and second leads have substantially similar center-to-center spacing of adjacent electrodes, and the stimulation electrodes of the third lead have a center-to-center spacing of adjacent electrodes that is approximately one half of the center-to-center spacing of adjacent electrodes of the first and second leads.

In a preferred exemplary version of the first embodiment, the plurality of stimulation electrodes for the first and second leads include the same number of electrodes, and the plurality of stimulation electrodes for the third lead includes double the number of electrodes for either the first or second leads. For example, the first and second leads may each include four stimulation electrodes, and the third lead may include eight stimulation electrodes.

In a second exemplary embodiment, an implantable neurostimulation lead kit may be provided for epidural spinal cord stimulation. The kit generally comprises first, second and third implantable electric stimulation leads, with each of the first, second and third leads having a distal end portion. Each of the first and second leads has a plurality of stimulation electrodes spaced apart along the distal end portion thereof wherein the plurality of stimulation electrodes of the first and second leads define a plurality of transverse pairs of stimulation electrodes. One stimulation electrode of each transverse pair is located on the first lead and the other stimulation electrode of each transverse pair being located on the second lead. Each transverse pair of stimulation electrodes is so located along the first and second leads that the transverse pair of stimulation electrodes is adapted to define a transverse line generally transverse relative to the spinal cord after implantation of the lead kit. The third lead has a plurality of longitudinal pairs of adjacent stimulation electrodes corresponding to the transverse pairs of transverse stimulation electrodes of the first and second leads wherein each such longitudinal pair of adjacent stimulation electrodes forms an electrode set with one of the transverse pairs of stimulation electrodes. A distal stimulation electrode of such longitudinal pair is positioned along the third lead such that the distal stimulation electrode is adapted to be displaced distally of the transverse line defined by the transverse pair of stimulation electrodes of that electrode set, and a proximal stimulation electrode of such longitudinal pair is positioned along the third lead such that the proximal stimulation electrode is adapted to be displaced proximally of the transverse line defined by the transverse pair of stimulation electrodes of that electrode set.

An exemplary method generally comprises percutaneously implanting the first, second and third leads in the epidural space of a patient, and programming the stimulation electrodes to create a tripole in which at least one electrode is active on each of the first, second and third lead. Preferably, voltage or current of each of the stimulation electrodes programmed in the programming step are independently controlled.

In a preferred example of the method, the position of the first, second and third leads is verified using imaging, such as fluoroscopy, such that the electrodes of the three leads are arranged in an array in which each electrode of the left or right lead has a longitudinal position (ignoring lateral coordinates) between the longitudinal positions to two adjacent electrodes of the center lead.

In a fourth exemplary embodiment, a method is provided for electrically stimulating the spinal cord with first, second and third electric stimulation leads. The method of the fourth exemplary embodiment generally comprises percutaneously implanting the first, second and third electric stimulation leads in the epidural space of a patient with: (1) the first, second and third leads forming a generally parallel lead array in the epidural space in which the third lead is disposed between the first and second leads, (2) the plurality of stimulation electrodes of the first and second electric stimulation leads defining a plurality of transverse pairs of stimulation electrodes, one stimulation electrode of each transverse pair being located on the first lead and the other stimulation electrode of each transverse pair being located on the second lead, such that each transverse pair of stimulation electrodes defines a transverse line generally transverse relative to the spinal cord; and (3) the plurality of stimulation electrodes of the third lead defining a plurality of longitudinal pairs of adjacent stimulation electrodes corresponding to the transverse pairs of transverse stimulation electrodes of the first and second leads, thus forming a plurality of electrode sets each defined by one longitudinal pair and one transverse pair. Within each set, a distal stimulation electrode of the longitudinal pair is positioned distally of the transverse line defined by the transverse pair of that electrode set and a proximal stimulation electrode of such longitudinal pair is positioned proximally of the transverse line defined by the transverse pair of that electrode set. The stimulation electrodes are programmed to create a tripole in which at least one electrode is active on each of the first, second and third lead within at least one of the electrode sets.

In a fifth exemplary embodiment, a method is provided for electrically stimulating the spinal cord with first, second and third electric stimulation leads. Each of the first, second and third leads may have a distal end portion with a plurality of stimulation electrodes space apart therealong. The stimulation electrodes of the first and second leads may have substantially similar center-to-center spacing of adjacent electrodes, and the stimulation electrodes of the third lead may have a center-to-center spacing of adjacent electrodes that is approximately one half of the center-to-center spacing of adjacent electrodes of the first and second leads. The method of the fifth exemplary embodiment generally comprises (a) implanting (e.g., percutaneously implanting) the first, second and third electric stimulation leads in the epidural space of a patient with (1) the first, second and third leads forming a generally parallel lead array in the epidural space in which the third lead is disposed between the first and second leads, and (2) the plurality of stimulation electrodes on the first, second and third electric stimulation leads form a plurality of electrode sets wherein each electrode set is arranged in a generally diamond-shaped array, (b) programming the stimulation electrodes to create a tripole in which at least one electrode is active on each of the first, second and third lead within at least one of the electrode sets. Each of the electrode sets formed in step (a)(2) comprises a transverse pair of stimulation electrodes, with one stimulation electrode of such transverse pair being on each of the first and second electric stimulation leads; and a longitudinal pair of stimulation electrodes on the third electric stimulation lead wherein the two stimulation electrodes of the longitudinal pair are adjacent one another.

In a sixth exemplary embodiment, a method is provided for electrically stimulating the spinal cord with a stimulation electrode array. The method generally comprises implanting the stimulation electrode array in the epidural space of a patient. The stimulation electrode array is arranged in first, second and third generally parallel columns with the third column being arranged between the first and second columns. Each of the first, second and third columns being formed by a plurality of stimulation electrodes with the stimulation electrodes of the first and second columns having substantially similar center-to-center spacing of adjacent electrodes, and the stimulation electrodes of the third column having a center-to-center spacing of adjacent electrodes that is approximately one half of the center-to-center spacing of adjacent electrodes of the first and second columns. The plurality of stimulation electrodes in the first, second and third columns form a plurality of electrode sets wherein each electrode set is arranged in a generally diamond-shaped array. Each electrode array comprises a transverse pair of stimulation electrodes, with one stimulation electrode of such transverse pair being located in the first column and the other stimulation electrode of the transverse pair being located n the second column, and a longitudinal pair of stimulation electrodes located in the third column wherein the two stimulation electrodes of the longitudinal pair are adjacent one another. The stimulation electrodes are programmed to create a tripole in which at least one electrode is active on each of the first, second and third columns within at least one of the electrode sets. In the sixth exemplary embodiment, it is contemplated that the electrode array could be formed by the use of one or more leads, such as for example use of three percutaneous leads, or by use of a single surgical paddle-style lead.

BRIEF DESCRIPTION OF THE DRAWINGS

FIGS. 17, 18 and 19 show tables A, B and C illustrating various exemplary electrode program configurations with either voltage or current controlled electrical waveforms, and each table includes an illustrative cross reference to the figures.

DETAILED DESCRIPTION OF EXEMPLARY EMBODIMENTS

Figure 1:
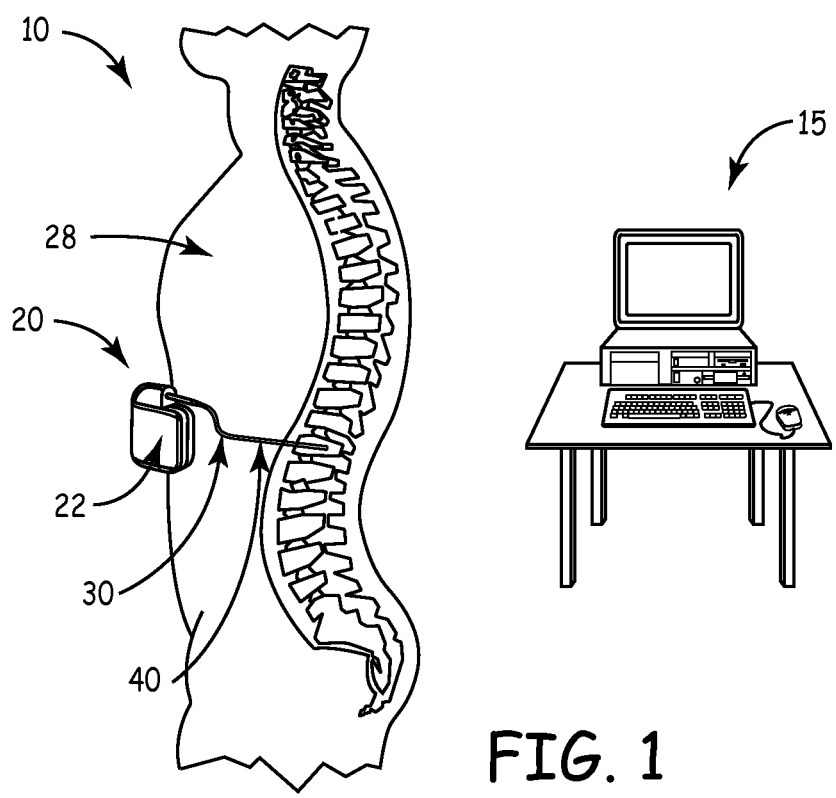
FIG. 1 shows a general environmental view for an embodiment of a neurostimulation system used to stimulate the spinal cord.
Figure 2:
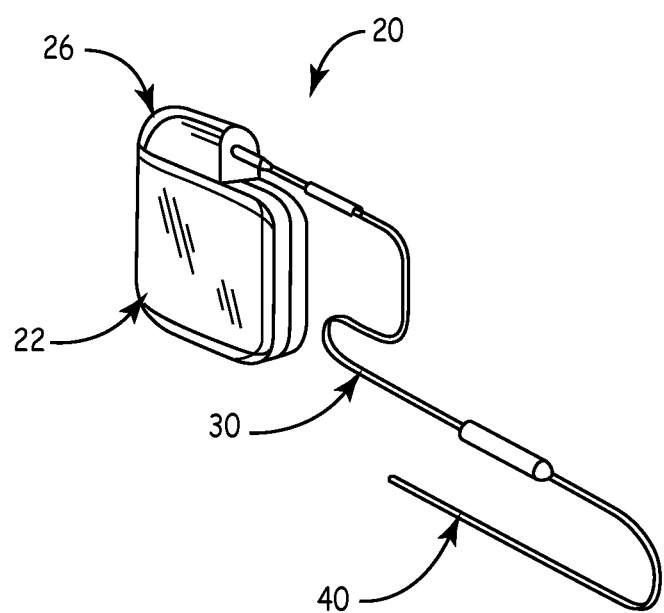
FIG. 2 shows the neurostimulation system of FIG. 1.
Figure 3:
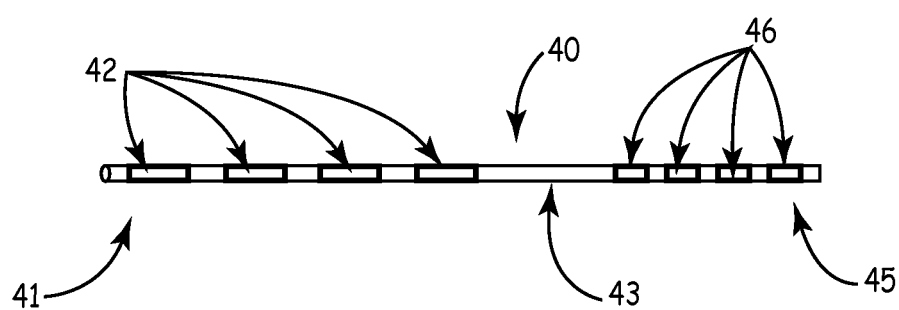
FIG. 3 shows an embodiment of a neurostimulation lead used in the neurostimulation system of FIGS. 1 and 2.

FIG. 1 shows a general environmental view 10 for an exemplary implantable neurostimulation system embodiment. Neurostimulation systems may be used to treat conditions such as pain, movement disorders, pelvic floor disorders, gastroparesis, and a wide variety of other medical conditions. As illustrated in FIGS. 1 and 2, the neurostimulation system 20 may include a neurostimulator 22, one or more stimulation lead extension(s) 30, and one or more stimulation lead(s) 40 (preferably three leads as illustrated in FIGS. 4-16). The neurostimulator 22 is typically implanted subcutaneously in the patient's body 28 at a location selected by the clinician. The stimulation lead 40 is typically fixed in place near the location selected by the clinician using a device such as an adjustable anchor.

The exemplary implantable neurostimulator 22 has a housing, a power supply in the housing 24, and stimulation electronics in the housing in electrical communication with the battery and in electrical communication with a connector block 26, which is also known as a terminal block.

The implantable neurostimulator 22 may be configured to provide current controlled pulses, voltage controlled pulses or both. The pulses are preferably independently variable (e.g., programmable) so that the voltage or current of each active electrode can be independently controlled. In current controlled embodiments (see, e.g., table C), it is contemplated that each electrode could be an independently controllable current source or independently controllable current sink. An alternative embodiment of a current controlled-type neurostimulator 22 may include one or more electrodes that are programmed to be a voltage reference with other electrodes programmed to be current sources or current sinks. Tables A and B illustrate some exemplary programs in which the electrodes are programmed in a voltage controlled scheme.

The exemplary stimulation lead 40 has a proximal end portion 45, a distal end portion 41 and a lead body 43 extending between the proximal end portion 45 and distal end portion 41. The proximal end portion 45 has at least one electrical connector 46 (also known as electrical terminals or contacts), with various standard pluralities, such as four or eight electrical contacts, being typical. The distal end portion 41 has at least one stimulation electrode 42, with various standard pluralities, such as four or eight electrodes, being typical.

At least one exemplary embodiment of the preferred stimulation leads includes such leads as are designed for percutaneous implantation, for example, through one or more needles. Such percutaneous leads typically have a generally cylindrical configuration with ring electrodes 42 in the distal end portion and ring contacts 46 in the proximal end portion. An alternative exemplary embodiment may involve use of a segmented or partial ring electrodes, each of which extends along an arc less than 360 degrees (e.g., 90-120 degrees) along the circumference of the lead.

In at least one preferred exemplary embodiment of the lead the diameter of the ring electrode is slightly smaller than the diameter of the adjacent area of the lead. This may help avoid direct contact between electrodes on adjacent leads. Alternatives include various structures or means, such as ribs, protuberances, flanges or bumps, that maintain some separation of electrodes on adjacent leads. Any such structure or arrangement constitutes an exemplary embodiment of a means for avoiding direct contact between electrodes on adjacent leads.

When used in the context of a lead, the term "longitudinal" refers to the direction of elongation of the lead, or to the substantially common direction of elongation of a plurality of substantially parallel leads (including without limitation leads placed alongside one another in the epidural space). "Lateral," when used in the context of a lead, refers to the direction generally perpendicular to the longitudinal direction of the lead or substantially parallel leads. When used in the context of the spinal cord, "longitudinal," "lateral" and "medial" are used in their common medically accepted meanings, e.g., "longitudinal" refers to the axial direction of the spinal cord. The term "transverse" when used in the context of a lead or electrode array relative to the spinal cord includes both the lateral direction relative to the spinal cord and diagonal directions relative to the spinal cord but in either case the term "transverse" implies some crossing over a center line or point defined with respect to the spinal cord or a central lead. All such terms are intended to have approximate practical meanings in view of the limp structure of exemplary preferred leads and the environment of use, rather than precise geometrical meanings.

In the context of a lead, "distal" means the longitudinal direction along the lead toward the free end of the lead (e.g., typically the end with tissue stimulating electrodes), and "proximal" refers to the longitudinal direction toward the end of the lead that is intended to be connected to an implantable neurostimulator 22, or a lead extension that is intended to connect the lead with such an neurostimulator 22. Because some exemplary leads may be typically somewhat flexible and limp such that the distal and proximal ends of the leads in a mechanical sense could be brought together, it will be understood that proximal and distal refer to relative positions along the length of the lead rather than a coordinate grid in absolute space.

There is at least one lead conductor 50 contained in the lead body 43 that is electrically connecting the electrical connector 46 to the stimulation electrode 42. Typically, at least one conductor may be used to establish electrical communication between a single electrical connector/electrode pair, although alternative examples include multiplexing or bus features within the lead to allow use of fewer conductors along the length of the lead than the number of electrodes. As used herein, "conductive means" or "means for electrical communication between electrodes and electrical connectors" include the foregoing examples or any alternative structure that allows selection or electrical activation of one or more electrode.

As used herein, "transverse tripole stimulation" or "TTS" refers to any arrangement in which at least three electrodes are arranged with a substantial transverse component relative to the neural tissue being stimulated (e.g., along a line that substantially departs from the longitudinal axis of the spine). Examples include without limitation (a) at least three co-linear, epidural electrodes arranged along one or more lead(s) in a line approximately perpendicular to the spinal cord axis, (b) at least three co-linear, epidural electrodes in a line skewed with respect to (i.e. substantially not parallel with) the longitudinal axis of the spinal cord to provide a substantial transverse component to the electrical field generated by the electrodes, and (c) at least three non co-linear, epidural electrodes that provide a substantial transverse component to the electrical field generated by the electrodes, as well as other arrangements in which at least three electrodes are arranged with a substantial transverse component relative to the neural tissue being stimulated.

"Outer" in the context of electrodes forming a tripole set refers to the outer electrodes forming the outer part of a tripole array where the "center" or "medial" electrode(s) form(s) the inner part of the tripole array. In the context of a transverse tripole, the spacing of the outer electrodes from the inner electrode(s) will include a lateral component, where lateral is defined relative to the spinal cord. The outer electrodes may also be referred to as either right or left electrodes.

Electrodes may also be identified by the following conventions: L0, L1, . . . , LN; C0, C1, . . . , CN; R0, R1, . . . , RN;

where "L" refers to an electrode on the left outer lead, "C" refers to an electrode on the center lead, and "R" refers to an electrode on the right outer lead. The associated numbering (e.g., L0 to LN) refers to an order starting at the distal end of the lead, with "N" refers to the number of electrodes on the lead minus 1. An alternative convention is to number the electrodes from E0 to EN, where "N" refers to the total number of electrodes connected to the neurostimulator 22 minus 1 (e.g., N=15 if the neurostimulator is designed to work with 16 electrodes). Other conventions may also be employed, and the described convention are merely provided as exemplary illustrations.

Use of the term, "adjacent" in connection with electrodes refers to electrodes within a configuration or array that are not separated by other electrodes, so "adjacent" electrodes may still be spaced apart or separated from one another. Examples of adjacent electrodes include electrodes L0 and L1 shown in FIG. 4, or electrodes L0 and C0 in FIG. 4.

In TTS, the electrical field can be steered from side to side by varying the current or voltage between the electrodes. Examples include without limitation varying the current or voltage of the two outer electrodes independently of each other, or independently varying the current or voltage between the center electrode(s) and outer electrodes. Voltages or currents may be in phase (overlapping in time) or out of phase between the right and left side.

Figure 4:
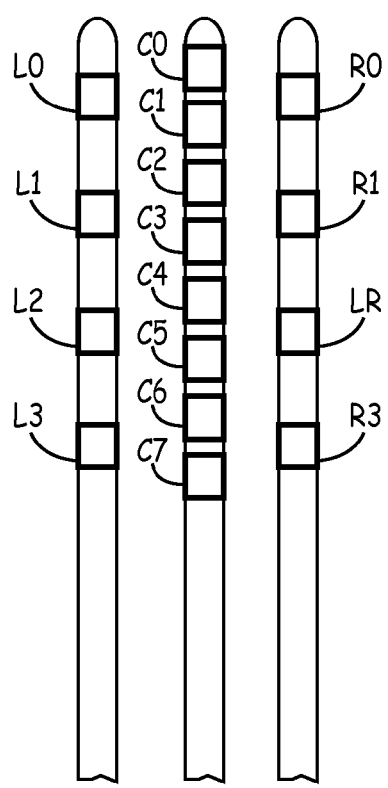
FIG. 4 shows an exemplary embodiment comprising three percutaneously-implanted epidural electrical-stimulation leads arranged is laterally spaced apart relationship.
Figure 5:
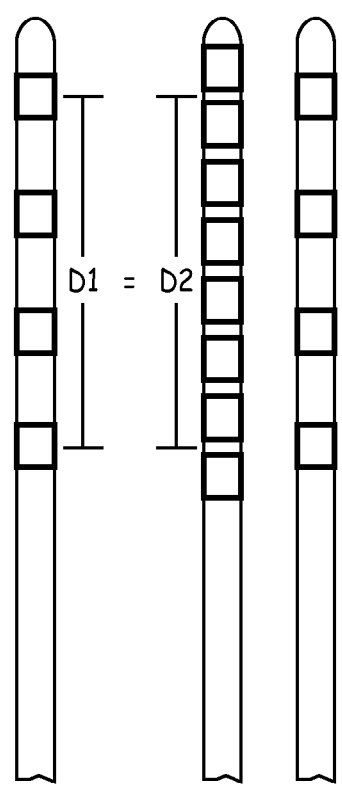
FIG. 5 shows the exemplary embodiment of FIG. 4 illustrating the relative spacing between electrodes in each lead relative to the other leads.

A first exemplary embodiment of transverse tripole stimulation ("TTS") may employ three leads: two four-electrode leads and one eight-electrode lead. Each four-electrode lead may have four electrodes that may be arranged in line along the longitudinal axis of a lead, and the eight-electrode lead may have eight electrodes that may be arranged in line along the longitudinal axis of a lead. This exemplary embodiment is illustrated in FIG. 4, with four electrodes L0, L1, L2 and L3 on the right lead; eight electrodes C0, C1, C2, C3, C4, C5, C6 and C7 on the central lead; and four electrodes R0, R1, R2 and R3 on the right lead. A second exemplary embodiment may include electrodes distributed as follows: five electrodes on the right and left leads, and six electrodes on the center lead. It will be understood that the number of electrodes in each lead and the total number of electrodes could be varied from these exemplary embodiments.

Most preferably, each lead in this exemplary embodiment is what is typically referred to as a percutaneous lead, that is, a lead that is designed to be implanted through the skin via a needle rather than by a more invasive cut-down procedure. As used in this context, a "percutaneous" lead may be fully implanted, that is, it does not imply that some portion of the lead extends through the skin following implantation. Typical examples of such leads include substantially cylindrical lead bodies, such as illustrated in the figures.

In the first exemplary embodiment (e.g., FIGS. 4-10), the relative spacing of electrodes in each of the three leads is selected such that the electrodes of the three leads match up in a symmetric way. This may be accomplished, for example, by having the distance $D_1$ between the centers of the outboard electrodes on the four-electrode leads equal to the distance $D_2$ between the centers of the outboard spaces on the eight-electrode lead, as shown in the FIG. 5. As used herein, "spaces" refers to the spaces between adjacent electrodes in a lead, and "outboard" refers to the longitudinal extremes, e.g., the distal most electrode (e.g., L0, C0, or R0), the proximal most electrode (e.g., LN, CN, or RN), the space between the distal most electrode and its adjacent electrode, or the space between the proximal most electrode and its adjacent electrode.

In the first exemplary embodiment, the electrode lengths and spaces may be consistent on each lead, although it may be preferred for the electrode lengths and spacing not to be equal between the four-electrode leads and the eight-electrode lead. For example, the four-electrode lead may have 3 mm length electrodes and 6 mm spaces between adjacent electrodes, whereas the eight-electrode lead may have 3.5 mm length electrodes and 1 mm spaces between adjacent electrodes. The term "adjacent" as used with respect to electrodes on the same lead does not refer to proximity per se (because adjacent electrodes may be separated by meaningful distances) but merely refers to the absence of intermediate electrodes between the adjacent electrodes.

Exemplary equations for determining an exemplary preferred relationship between leads in a 4-8-4 electrode lead embodiment include the following:

$S_E$=space between adjacent electrodes in lead
$L_E$=length of electrode in lead $$D_1 = 3 \times S_E + 3 \times L_E \text{ (four-electrode leads)}$$

$$D_2 = 6 \times S_E + 6 \times L_E \text{ (eight-electrode lead)}$$

$$D_1 = D_2$$

For example, one exemplary preferred embodiment may include two four-electrode leads with 3 mm length electrodes and 6 mm spacing between electrodes, and one eight-electrode lead with 3 mm length electrodes and 1.5 mm spacing between adjacent electrodes:

For $D_1$: $L_E$=3 mm; $S_E$=6 mm
For $D_2$: $L_E$=3 mm; $S_E$=1.5 mm $$D_1 = 3 \times 6 + 3 \times 3 = 27$$

$$D_2 = 6 \times 1.5 + 6 \times 3 = 27$$

$$D_1 = D_2$$

Alternatively, a second exemplary preferred embodiment may include a four-electrode lead with 3 mm length electrodes and 4 mm spacing between adjacent electrodes, and an eight electrode lead with 2.5 mm length electrodes and 1.0 mm spacing between electrodes:

For $D_1$: $L_E$=3 mm; $S_E$=4 mm
For $D_2$: $L_E$=2.5 mm; $S_E$=1.0 mm $$D_1 = 3 \times 4 + 3 \times 3 = 21$$

$$D_2 = 6 \times 1 + 6 \times 2.5 = 21$$

$$D_1 = D_2$$

An alternative exemplary equation involves employing outer leads having twice the center-to-center spacing between adjacent electrodes than employed in the center lead. As used in this context with a cylindrical lead having ring electrodes, the "center" of an electrode means the circumferential centerline of the electrode that is approximately perpendicular to the longitudinal axis of the lead. For example, if the electrode length $L_E$=3 mm and the spacing between electrodes $S_E$=4 mm for an outer or side lead, the center-to-center spacing would be 7 mm. In that case a preferred exemplary embodiment of the center lead would include electrodes having a length $L_E$=2.5 mm and spacing between electrodes $S_E$=1.0 mm, in which case the center-to-center spacing of the adjacent electrodes would be 3.5 mm (one half of the 7 mm spacing of the exemplary center-to-center electrode spacing of the outer or side leads).

Whether to have the most cathodal electrode as the center electrode of the tripole set, or on one end, is a choice of the physician, and may or may not have a significant impact on the effects of electric stimulation. Using the outer electrodes as anodes, however, may avoid nerve root stimulation.

Tables A, B and C, provided as FIGS. 17-19, include cross references to one or more of FIGS. 6-16, and may be referred to for further illustration of the examples outlined with respect to FIGS. 6-16. Table A (FIG. 17) illustrates various exemplary electrode programs for voltage controlled stimulation; Table B (FIG. 18) illustrates various exemplary electrode programs for voltage controlled stimulation in which cathodal voltage is less than the shield/housing voltage of the neurostimulator 22; and Table C (FIG. 19) illustrates various exemplary electrode programs for current controlled stimulation.

Figure 6:
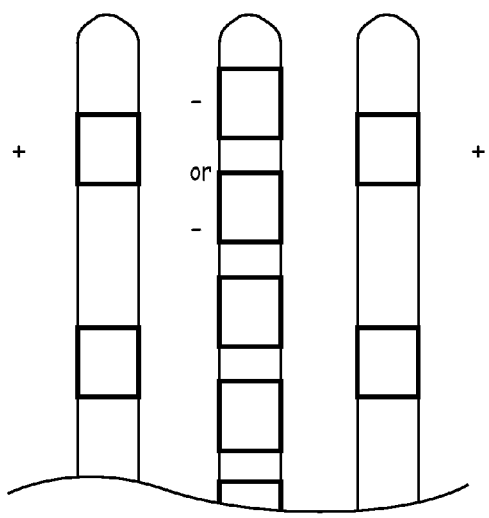
FIG. 6 illustrates an exemplary embodiment in which three leads are arranged in a laterally spaced-apart array with a moderately longitudinally skewed active electrodes selected.
Figure 7:
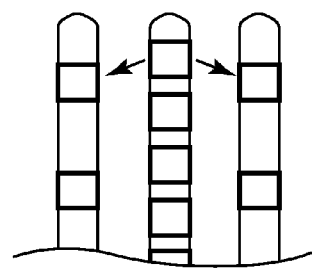
FIG. 7 illustrates the exemplary embodiment of claim 6 with arrows indicating direction of electron flow, which, while applicable to both voltage controlled and current controlled devices, is particularly shown to illustrate current controlled embodiments.
Figure 8:
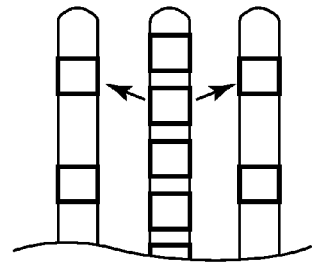
FIG. 8 is similar to FIG. 7 with an alternative selection of a central electrode.

As illustrated in FIGS. 6-8, the two indicated alternative center electrodes (which may be used, e.g., as cathodes) may be slightly offset longitudinally from the outer electrodes (which may be used, e.g., as anodes), thereby increasing the longitudinal component to the electric field generated between the active center electrodes and active outer electrodes. This may help to reduce the amount of electrical energy required for paresthesia, since a longitudinal component of the activating function provides dorsal column stimulation. FIG. 6 includes symbols (+ or −) indicating an exemplary selection of polarity of the active electrodes, and FIGS. 7 and 8 include arrows indicating alternative exemplary directions of electron flow.

Figure 9:
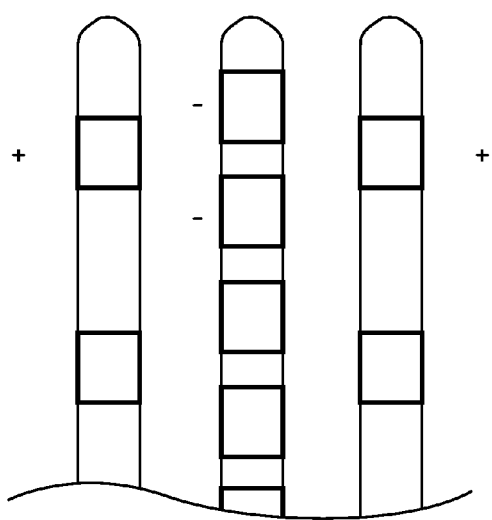
FIG. 9 illustrates an embodiment in which the three leads of FIGS. 6 and 7 have non-skewed active electrodes selected generally perpendicular to the axis of the spinal cord (also perpendicular to the axes of the leads) with two center electrodes selected.
Figure 10:
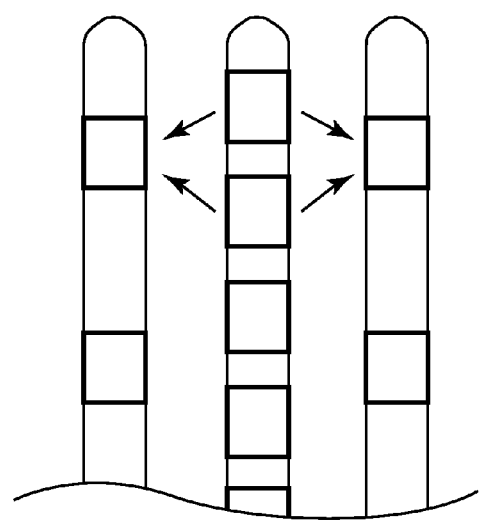
FIG. 10 illustrates the exemplary embodiment of claim 8 with arrows indicating direction of electron flow, which, while applicable to both voltage controlled and current controlled devices, is particularly shown to illustrate current controlled embodiments.

As illustrated in FIGS. 9 and 10, transverse tripole fields may be created by using a pair of central electrodes (e.g., as cathodes). Since epidural electrodes may be at least 2-5 mm away from the spinal cord, if two neighboring electrodes are cathodal, the net effect is substantially like having a single cathode at the center of the pair, or if the neighboring electrodes are anodal, the net effect is substantially like having a single anode at the center of the pair. FIG. 9 includes symbols (+ or −) indicating exemplary polarities of the active electrodes. FIG. 10 includes arrows indicating an exemplary direction of electron flow.

Figure 11:
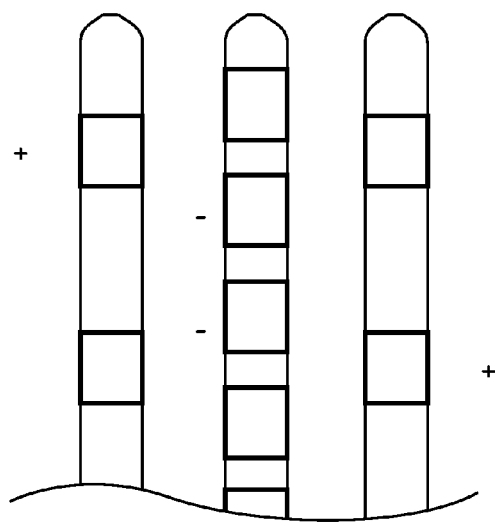
FIG. 11 illustrates an embodiment in which the three exemplary leads of FIGS. 6-10 have skewed active electrodes selected with a greater degree of skewing than FIG. 6-8.
Figure 12:
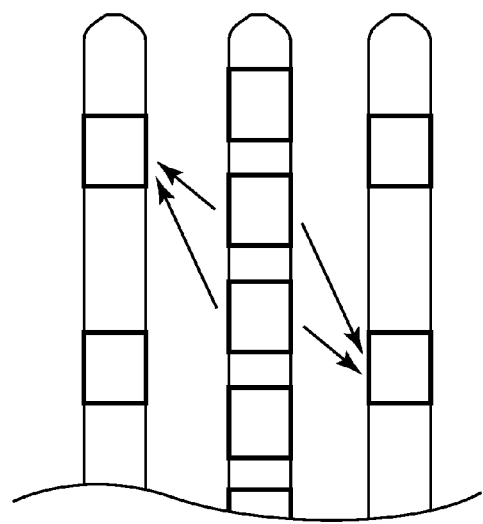
FIG. 12 illustrates the exemplary embodiment of claim 11 with arrows indicating direction of electron flow, which, while applicable to both voltage controlled and current controlled devices, is particularly shown to illustrate current controlled embodiments.

As illustrated in FIGS. 11 and 12, skewed tripole stimulation may be performed (more skewed than FIGS. 6-8). In skewed tripole stimulation, the outer electrodes are not at the same longitudinal location, and one or two cathodes on the middle lead are between the outer two electrodes used. FIG. 11 includes symbols (+ or −) indicating exemplary polarities of the active electrodes. FIG. 12 includes arrows indicating an exemplary direction of electron flow.

Figure 13:
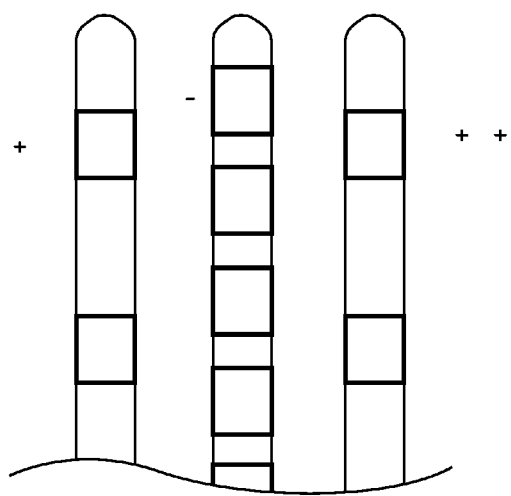
FIG. 13 illustrates an embodiment in which the three leads of FIGS. 6-12 have active electrodes selected and provided with pulses of different voltage amplitudes (e.g., the right outer electrode has a greater amplitude voltage pulse than the left outer electrode), illustrating independent control and electric field steering using a voltage controlled scheme.
Figure 14:
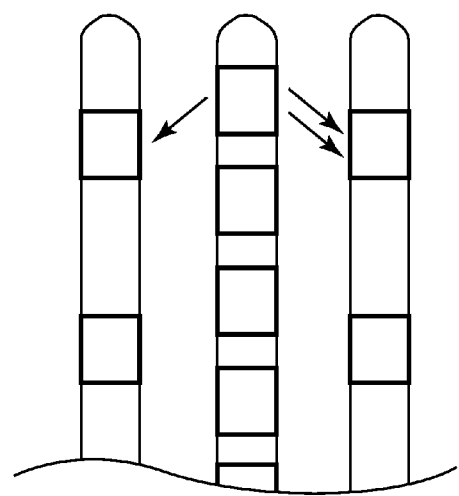
FIG. 14 is similar to FIG. 13 except that different amplitude current pulses are provided to the outer electrodes, illustrating independent control and field steering using a current controlled scheme.

FIGS. 13 and 14 illustrate an exemplary programming embodiment in which the electrodes are programmed for field steering. Field steering may be accomplished, for example, by varying the relative (anodal or cathodal) voltage or current of the outer electrodes. FIG. 13 includes symbols (+ or −) indicating exemplary polarity and relative voltages of the active electrodes. FIG. 14 includes arrows indicating an exemplary directions and relative amplitudes of electron flow.

Figure 15:
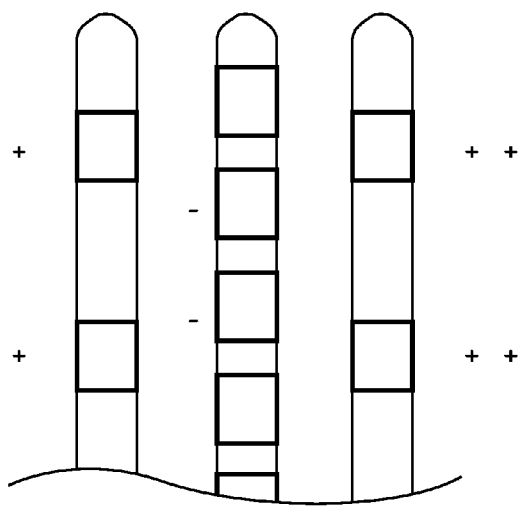
FIG. 15 illustrates an embodiment in which the three leads of FIGS. 6-14 have additional electrodes selected in a non-skewed active array to form a wider field than in the embodiments of FIGS. 6-14 and in which different amplitude voltage pulses are provided to the outer electrodes to steer the electric field generated by the electrodes.
Figure 16:
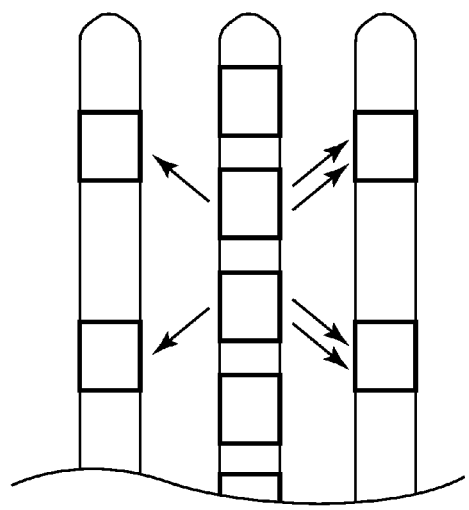
FIG. 16 is similar to FIG. 15 except that different amplitude current pulses are provided to the outer electrodes, illustrating independent control and field steering using a current controlled scheme.

FIGS. 15 and 16 illustrate a wide-field programming exemplary embodiment of TTS with field steering. In this exemplary embodiment, two adjacent electrodes on each outer lead and two adjacent electrodes on the central lead are shown as active to provide a wider field, and the voltage or current amplitude of the electrodes on the right lead are shown as relatively greater than the left lead. FIG. 15 illustrates exemplary polarities and relative voltage amplitude of the active electrodes of this embodiment as carried out in a voltage controlled scheme, and FIG. 16 includes arrows indicating exemplary directions and relative amplitudes or electron flow that may be considered as illustrating both current controlled and voltage controlled schemes.

Current-controlled electrical pulses typically have a constant current (I) delivery during the duration of the pulse (pulse width or "PW"). Alternatively, wave-shaping could be used to allow delivery of a changing current during the pulse. Of course, there will be a following pulse of opposite sign at each electrode to keep the net charge delivered zero over time.

Voltage-controlled pulses typically have a constant (V) or decreasing voltage amplitude (V(t)) during the duration of the pulse. Decreasing voltage amplitude over time is common when the pulse comes from a discharging capacitor. Alternatively, wave-shaping techniques could be used to give a V(t) shape that varies during the pulse.

Any system of electrodes that delivers electrical pulses to the body typically include at least one cathode (negative, source of electrons) and at least one anode (positive, source of cations) to have a complete circuit of finite resistance in which currents may flow. When there are only two active electrodes, one is a cathode and one is an anode. Generally, activation of living cells is believed to occur under the cathode (because the negative fields are similar to the negative potential inside a cell, so the trans-membrane potential difference becomes less, until threshold is reached and an action potential begins). Action potentials may also happen at anodes, for example, when a long pulse (typically 1 msec long) ends so the voltage change near the anode becomes depolarizing, or whenever the recharge phase of a pulse for charge balance has a large, rapidly changing amplitude.

When there are three or more active electrodes, and the electrical pulses leaving them are overlapping in time for at least part of their cycle or PW, then electric fields can become complex. A device that delivers current-controlled pulses may have the ability to deliver part of the current, with controlled amplitude, to each chosen anode or cathode. During a pulse, the sum of all outward currents (and charges delivered) would ideally equal the sum of all ingoing currents (and charges brought back). The same is true during the recharge phases, for net charge balance.

Tripoles as discussed in this application are believed to be particularly useful for activating tissue. For example, use of one electrode for a cathodal pulse (either current- or voltage-controlled) and two electrodes that are anodal (also either current- or voltage-controlled), may be used, for example, in spinal cord stimulation, such as used as a therapy for pain. The area in which axons are excited may be limited by the hyperpolarization that occurs near the anodes. As amplitude is increased or decreased, the locus of recruited axons will go farther or nearer to the cathode, but the anodes may tend to shield neural structures beyond the anodes thus tending to prevent their stimulation. If done in a rostral/caudal direction, then it may be comparatively easy to recruit dorsal column fibers. If done in a medial/lateral direction, then it may be comparatively easy to recruit dorsal root fibers.

Since electrodes for spinal cord stimulation tend to be several millimeters away from spinal cord axons, with intervening low impedance cerebrospinal fluid, effects from various electrode combinations and polarities might be sufficiently attenuated that switching electrodes in or out of circuits might not have major effects. For cases where electrodes are very near axons (peripheral nerve stimulation, deep brain stimulation), it may be more important that bringing electrodes into or out of circuits should be done with control of each electrode's impedance, for example, with a series controllable resistor.

In one exemplary embodiment, a method is provided of electrically stimulating the spinal cord with exemplary first, second and third electric stimulation leads of the type described above. Each of the first, second and third leads has a distal end portion with a plurality of stimulation electrodes space apart therealong. The stimulation electrodes of the first and second leads may have substantially similar center-to-center spacing of adjacent electrodes, and the stimulation electrodes of the third lead may have a center-to-center spacing of adjacent electrodes that is approximately one half of the center-to-center spacing of adjacent electrodes of the first and second leads.

The first, second and third electric stimulation leads may be implanted, e.g., via a percutaneous implantation procedure, in the epidural space of a patient such that (1) the first, second and third leads form a generally parallel lead array in the epidural space in which the third lead is disposed between the first and second leads, and the plurality of stimulation electrodes of the first, second and third electric stimulation leads form a plurality of electrode sets wherein each electrode set is arranged in a generally diamond-shaped array. Each electrode set is formed by a transverse pair of stimulation electrodes, one stimulation electrode of such transverse pair being on each of the first and second electric stimulation leads; and a longitudinal pair of stimulation electrodes on the third electric stimulation lead wherein the two stimulation electrodes of the longitudinal pair are adjacent one another. Any combination of different electrode sets may share some but not all of the electrodes with each other. The stimulation electrodes may then be programmed to create a tripole in which at least one electrode is active on each of the first, second and third lead within at least one of the electrode sets.

It is contemplated that the plurality of electrode sets in a preferred exemplary embodiment may take at least two forms, one of which may be referred to as a first electrode set or as having a "pure" or "perfect" transverse pair, and other of which may be referred to as a second electrode set, which has a transverse pair extending diagonally. As used herein, the terms "pure" and "perfect" are merely used as non-limiting labels to provide a distinction relative to exemplary diagonal pairs, and not intended to convey a standard of purity or perfection. In first electrode sets, the transverse pair of each first electrode set defines a transverse line that is generally perpendicular relative to the spinal cord. In the second electrode sets, the transverse pair defines a transverse line that is generally diagonal relative to the spinal cord. Any combination of a first electrode set and second electrode set may share some but not all of the stimulation electrodes of the first and second electrode sets of the combination.

The stimulation electrodes of at least one of the first or second electrode sets may be programmed as active. Programs are also contemplated in which more than one electrode set is programmed as active, or in which only one electrode set is programmed as active.

For example, the stimulation electrodes of at least one of the first electrode sets may be programmed as active. In this case, all of the stimulation electrodes of such first electrode set may be programmed as active to provide a transverse electric field oriented generally perpendicular to with respect to the spinal cord as illustrated in FIGS. 9 and 10, or only one of the stimulation electrodes of the longitudinal pair of the first electrode set may be programmed as active to provide a transverse electric field having a longitudinal component but otherwise oriented generally perpendicular to with respect to the spinal cord as illustrated in FIGS. 6-8.

As another example, the stimulation electrodes of at least one of the second electrode sets may be programmed as active. In this case, all of the stimulation electrodes of such second electrode set may be programmed as active as illustrated in FIGS. 11 and 12, or only one of the stimulation electrodes of the longitudinal pair of such second electrode set may be programmed as active (e.g., make one of the active stimulation electrodes of the central lead shown in FIGS. 11 and 12 inactive).

Medical imaging techniques, such as fluoroscopy, may be used to verify the position of the first, second and third electric stimulation leads. For example, the position of the first, second and third leads may be verified using imaging such that the stimulation electrodes of the three leads are arranged in an array in which each electrode of the left or right lead has a longitudinal position (ignoring lateral coordinates) between the longitudinal positions to two adjacent electrodes of the center lead.

The third electric stimulation lead (central lead) may be implanted, for example, before implanting the first and second electric stimulation leads (right and left leads). Medical imaging techniques may be employed to determine the distance between the distal portion of the central electric stimulation lead and the spinal cord. The distal portions of the first and second electric stimulation leads in this example may then be placed in the epidural space of a patient, each at a distance from the distal portion of the third electric stimulation lead about the same as the distance between the distal portion of the third lead and the spinal cord. Medical imaging techniques may then be used to determine the distance between the distal portion of the first and second leads from the third lead, and verify that such distance is about the same as the distance between the distal portion of the third lead and the spinal cord. This arrangement is believed to be advantageous for providing electrical stimulation to the spinal cord as part of a pain management therapy.

Medical imaging techniques may also be used to verify that the first electrode sets are arranged in a pattern relative to the spinal cord in which the transverse lines defined by the transverse pairs of the first electrode sets are actually reasonably close to perpendicular relative to the spinal cord.

Thus, exemplary embodiments of the TRANSVERSE TRIPOLE NEUROSTIMULATION METHODS AND SYSTEMS are disclosed. The disclosed embodiments are presented for purposes of illustration and not limitation.

What is claimed is:

1. A method of electrically stimulating the spinal cord with first, second and third electric stimulation leads, each of the first, second and third leads having a distal end portion with a plurality of stimulation electrodes therealong, the method comprising:
 (a) percutaneously implanting the first, second and third electric stimulation leads in the epidural space of a patient with:
  (1) the first, second and third leads forming a generally parallel lead array in the epidural space in which the third lead is disposed between the first and second leads,
  (2) the plurality of stimulation electrodes of the first and second electric stimulation leads defining a plurality of transverse pairs of stimulation electrodes, one stimulation electrode of each transverse pair being located on the first lead and the other stimulation electrode of each transverse pair being located on the second lead, such that each transverse pair of stimulation electrodes defines a transverse line generally transverse relative to the spinal cord; and
  (3) the plurality of stimulation electrodes of the third lead defining a plurality of longitudinal pairs of adjacent stimulation electrodes corresponding to the transverse pairs of transverse stimulation electrodes of the first and second leads, thus forming a plurality of electrode sets each defined by one longitudinal pair and one transverse pair, wherein within each set
  (i) a distal stimulation electrode of the longitudinal pair is positioned distally of the transverse line defined by the transverse pair of that electrode set and
  (ii) a proximal stimulation electrode of such longitudinal pair is positioned proximally of the transverse line defined by the transverse pair of that electrode set; and
(b) programming the stimulation electrodes to create a tripole in which at least one electrode is active on each of the first, second and third lead within at least one of the electrode sets.

2. The method of claim 1 in which the plurality of electrode sets forms:
  a plurality of first electrode sets in which the transverse pair defines a transverse line that is generally perpendicular relative to the spinal cord; and
  a plurality of second electrode sets in which the transverse pair defines a transverse line that is generally diagonal relative to the spinal cord;
  wherein any combination of a first electrode set and second electrode set may share some but not all of the stimulation electrodes of the first and second electrode sets of the combination; and
  wherein the step of programming the stimulation electrodes to create a tripole in which at least one electrode is active on each of the first, second and third lead within at least one of the electrode sets includes programming active stimulation electrodes of at least one of the first or second electrode sets.

3. The method of claim 2 in which the step of programming active stimulation electrodes of at least one of the first and second electrode sets includes programming active stimulation electrodes of at least one of the first electrode sets.

4. The method of claim 3 in which the step of programming active stimulation electrodes of at least one of the first electrode sets includes programming all of the stimulation electrodes of such first electrode set as active to provide a transverse electric field oriented generally perpendicular to with respect to the spinal cord.

5. The method of claim 3 in which the step of programming active stimulation electrodes of at least one of the first electrode sets includes programming the stimulation electrodes of the transverse pair and only one of the stimulation electrodes of the longitudinal pair of such first electrode set as active to provide a transverse electric field having a longitudinal component but otherwise oriented generally perpendicular to with respect to the spinal cord.

6. The method of claim 2 in which the step of programming active stimulation electrodes of at least one of the first and second electrode sets includes programming active stimulation electrodes of at least one of the second electrode sets.

7. The method of claim 6 in which the step of programming active stimulation electrodes of at least one of the second electrode sets includes programming all of the stimulation electrodes of such second electrode set as active.

8. The method of claim 6 in which the step of programming active stimulation electrodes of at least one of the second electrode sets includes programming the stimulation electrodes of the transverse pair and only one of the stimulation electrodes of the longitudinal pair of such second electrode set as active.

9. The method of claim 1 further comprising using medical imaging techniques to verify the position of the first, second and third electric stimulation leads.

10. The method of claim 9 in which:
  step (a) includes implanting the third electric stimulation lead before implanting the first and second electric stimulation leads;
  the step of using medical imaging techniques to verify the position of the first, second and third electric stimulation leads includes determining the distance between the distal portion of the third electric stimulation lead and the spinal cord; and
  step (a) further including positioning the distal portion of the first and second electric stimulation leads in the epidural space of a patient each at a distance from the distal portion of the third electric stimulation lead about the same as the distance between the distal portion of the third lead and the spinal cord.

11. The method of claim 10 in which the step of using medical imaging techniques to verify the position of the first, second and third electric stimulation leads further includes determining the distance between the distal portion of the first and second leads from the third lead and verifying that such distance is about the same as the distance between the distal portion of the third lead and the spinal cord.

12. The method of claim 11 in which the step of using medical imaging techniques to verify the position of the first, second and third electric stimulation leads includes verifying that the first electrode sets are arranged in a pattern relative to the spinal cord in which the transverse lines defined by the transverse pairs of the first electrode set are actually reasonably close to perpendicular relative to the spinal cord.

13. The method of claim 1 in which voltage or current of each of the stimulation electrodes programmed in the programming step are independently controlled.

14. The method of claim 13 in which voltage or current of at least two of the stimulation electrodes programmed in the programming step are independently controlled to provide field steering.

15. The method of claim 14 in which voltage or current of at least one of the stimulation electrodes of the first electric stimulation lead and at least one of the stimulation electrodes of the second electric stimulation lead are programmed in the programming step are independently controlled to provide field steering.

* * * * *